United States Patent [19]

Jensen

[11] Patent Number: 4,805,612

[45] Date of Patent: Feb. 21, 1989

[54] HIGH FREQUENCY VENTILATION

[75] Inventor: Robert L. Jensen, San Antonio, Tex.

[73] Assignee: SensorMedics Corporation, Anaheim, Calif.

[21] Appl. No.: 113,641

[22] Filed: Oct. 26, 1987

Related U.S. Application Data

[60] Division of Ser. No. 776,014, Sep. 13, 1985, Pat. No. 4,719,910, which is a continuation-in-part of Ser. No. 728,146, Apr. 29, 1985, abandoned, which is a continuation of Ser. No. 519,387, Aug. 1, 1983, abandoned, which is a continuation-in-part of Ser. No. 485,900, Apr. 18, 1983, abandoned, which is a continuation-in-part of Ser. No. 358,648, Mar. 16, 1982, abandoned.

[51] Int. Cl.⁴ ............................................. A61M 16/00
[52] U.S. Cl. ......................... 128/204.21; 128/205.18; 128/204.25
[58] Field of Search .................. 128/204.25, 204.21, 128/205.3, 204.23, 204.18, 205.18, 205.24

[56] References Cited

U.S. PATENT DOCUMENTS

| | | | |
|---|---|---|---|
| 3,225,758 | 12/1965 | March | 128/205.18 X |
| 3,863,082 | 1/1975 | Gillett et al. | 128/205.18 X |
| 4,076,021 | 2/1978 | Thompson | 128/205.18 |
| 4,592,349 | 6/1986 | Bird | 128/205.24 X |

FOREIGN PATENT DOCUMENTS 2635532  2/1977  Fed. Rep. of Germany ..................... 128/204.21

*Primary Examiner*—Edward M. Coven
*Attorney, Agent, or Firm*—Cox & Smith, Incorporated

[57] ABSTRACT

A high frequency oscillating ventilator. A flow of gas is conducted from a gas source to a high frequency oscillator. The high frequency oscillator comprises a housing including a magnet and having a diaphragmetically sealed piston mounted therein, an inlet connecting the space within the housing on the first side of the diaphragm to the gas conducting means, and a coil mounted to the first side of the diaphragm. Circuitry is provided which is operable to reverse the polarity of the flow of the current in the coil, thereby causing the diaphragm to move back and forth within the housing. A tube connecting the space on the second side of the diaphragm to the gas source and the patient's airway is provided. Also disclosed is a method of ventilating a patient with the high frequency oscillating ventilator, and a double lumen endotracheal tube for use in connection therewith.

10 Claims, 8 Drawing Sheets

HIGH FREQUENCY VENTILATION

CROSS REFERENCE TO RELATED APPLICATIONS

This application is a divisional application of co-pending application Ser. No. 776,014 filed on Sept. 13, 1985, now U.S. Pat. No. 4,719,910. Application Ser. No. 776,014 is itself a continuation-in-part application of co-pending application Ser. No. 728,146, filed on Apr. 29, 1985, and now abandoned, which is a continuation application of application Ser. No. 519,387, filed on Aug. 1, 1983, and now abandoned, which is a continuation-in-part application of application Ser. No. 485,900, filed on Apr. 18, 1983, and now abandoned, which is a continuation-in-part application of application Ser. No. 358,648, filed on Mar. 16, 1982, which is also now abandoned. The disclosure contained in those applications Ser. Nos. 728,146, 519,387, 485,900, and 358,648 are hereby incorporated into this application in their entirety by this specific reference thereto.

BACKGROUND OF THE INVENTION

1. Field of the Invention

The present invention relates generally to ventilators for supporting ventilation in air breathing animals. More particularly, the present invention relates to high frequency ventilators which operate by oscillating respiratory air supplied to a patient at a frequency above the normal breathing frequency of the patient.

2. Discussion of Related Art

The use of a medical apparatus to facilitate breathing in mammals is well known in the art. The apparatus may take the form of a simple oxygen mask or tent which supplies oxygen at slightly above atmospheric pressure. Such devices merely assist a person to breathe.

Ventilators which operate at a high frequency have been suggested in the past. There are three types of high frequency ventilators known in the art, the flow interrupter, the jet ventilator and the high frequency oscillating ventilator. The latter, as exemplified by U.S. Pat. No. 2,918,917 to Emerson, employs a reciprocating diaphragm to vibrate a column of gas supplied to a patient. The vibration is in addition to the subject's respiration, natural or artificial, and at a much more rapid rate, for example, from 100 to more than 1500 vibrations per minute. The Emerson apparatus is primarily designed to vibrate the patient's airway and organs associated therewith, although Emerson also recognized that high frequency vibration causes the gas to diffuse more rapidly within the airway and therefore aids the breathing function. However, the Emerson apparatus is incapable of supporting full ventilation of the patient and must be used in conjunction with the patient's spontaneous breathing or with another apparatus which produces artificially induced inhalation and exhalation.

The second type of high frequency ventilator, the flow interrupter, uses a valve to switch a high pressure source of gas on and off. There are three disadvantages to such a device. First, there is the hazard of having the valve stick in the open position, thereby exposing the patient to very high pressure. The other problems relate to the fact that the respiratory gas enters the trachea at high speed. The high speed causes erosion and burning of the trachea at the point of entry. Further, all the external energy applied to the patient is toward inspiration, driving mucus and secretions down further the lungs and relying solely on the compliance of the lungs and chest muscles for expiration. Consequently, the flow interrupter is of little value at frequencies over 3 Hz, which is the approximate limit of compliance of the lungs and chest muscles.

A third type of high frequency ventilator is the jet pulse ventilator as exemplified in U.S. Pat. No. 4,265,237 to Schwanbom et al. The Schwanbom et al. ventilator produces high frequency, high pressure pulses of air which are capable of fully ventilating a patient. According to the specification of that patent the respiration pulse developed by that ventilator arrives at the closing valve with a pressure of 0.2 bar (209 cm $H_2O$) to 2.7 bar (2797.2 cm $H_2O$). This pressure is sufficient to expand the lungs during inspiration. Expiration is caused by the natural compliance of the lungs and chest rebound after the jet of air is stopped Accordingly, it can be seen that the device described in the Schwanbom et al. patent must rely on the compliance of the lungs in order to ventilate the patient. If the lung compliance is low, greater pressure must be used. The device described in the Schwanbom et al. patent also supplies a source of lower pressure gas for spontaneous breathing by the patient. While such jet pulse ventilators are useful for some applications, they are not generally applicable and their use is limited to certain applications. For instance, when used to support the respiration of neonates, as, for instance, those suffering from hyaline membrane disease, the baby often suffers substantial injury to the airway due to erosion caused by the impact of the high velocity jet of gas on the airway. Further, like the flow interrupter, all the energy applied to the patient is during inspiration, causing secretions to be driven down into the lungs.

U.S. Pat. No. 4,155,356 to Venegas discloses a respiration assisting apparatus using high frequency pulses to hold a patient's airway open while the patient is breathing or being ventilated with a volume ventilator. As with the Emerson device, Venegas is not capable of fully supporting a patient and must rely either on the natural respiration cycle or on a volume type ventilator to sustain the patient.

It is believed that normal breathing functions of air breathing animals are caused by expansion of the chest cavity. The expansion puts a negative pressure on the outside of the plurality of alveolar sacs in the lungs. The innumerable alveolar sacs receive air from the tidal flow or air movements generated, replenishing the sacs with oxygen-containing gas and removing carbon dioxide-containing gas. The intake of oxygen into the body is referred to as oxygenation, and the elimination of carbon dioxide from the body is referred to as ventilation. The compliance of the alveolar sacs causes them to inflate and deflate in response to the pressure changes.

When the chest cavity expands and creates a negative pressure on the outside of the alveolar sacs, it is believed this causes the sacs to inflate and provides movement of air into the alveolar sacs due to the pressure change. In order to exhale, the pressure on the outside of the alveolar sacs is increased by relaxing the chest cavity, allowing the elastic alveolar sacs to reduce their size and allowing expiration.

As far as is known, commercially available prior art ventilators use a relatively high positive air pressure to inflate the lungs like a balloon until either a predetermined volume of air is delivered to the patient or a predetermined pressure is reached The operation and use of conventional mechanical ventilators is summarized in Kestner, J., "The Mechanical Ventilator", in C. C. Rattenborg (Ed.), *Clinical Use of Mechanical Ventilation*, Year Book Medical Publishers, Inc. (1981), pp. 46-60. If too much volume or pressure is utilized, the compliance or elasticity of the alveolar sacs is reduced. Eventually, the damage will become so extensive that the sacs will no longer function to expel gas and thereby provide oxygen and carbon dioxide exchange When a patient is hooked up to a ventilator, blood gases are -monitored to determine whether sufficient oxygenation and ventilation is occuring at the alveolar sacs. When the blood gases deteriorate, present ventilators must correct the problem by increasing the pressure of the gas flowing into the lungs. The increase in pressure affects the compliance and elasticity of the sacs even more and can eventually destroy the lungs. A person essentially becomes dependent upon the ventilator and must gradually be weaned from the ventilator.

When the patient's lungs are not diseased, a low inspiratory pressure can be used because the lungs can expand and contract on their own to provide volume exchange of gases in the alveolar sacs. When there is lung disease present, it may not be possible for the lungs to provide adequate ventilation or gas exchange in the alveolar sacs. This requires some means of facilitating the gas exchange.

The failure of ventilation in conventionally available ventilators generally begins with expiration failures. As mentioned earlier, the conventional method for increasing gas exchange when blood gases deteriorate is to increase the pressure of the gas flowing into the lungs. The lungs can sustain a slight over-pressuring for a short period of time and not incur permanent damage. However, continued over-pressuring will cause a change in the compliance of the alveolar sacs. A bleb or rupture can occur when the alveolar sac has exceeded its elastic limit. Hemorrhaging may result, which destroys .the ability of the sac to effect gas exchange and may cause other complications.

During normal breathing, it is believed that the alveolar sacs gradually deflate until they are no longer providing adequate gas exchange. In order to reinflate the alveolar sacs, an individual must sigh, reinflating the alveolar sacs to their full size. Failure to periodically sigh can be fatal because normal breaths allow the alveolar sacs to slowly deflate.

SUMMARY OF THE INVENTION

An object of the present invention is to provide a ventilator which will produce sufficient gas exchange to sustain full oxygenation and ventilation of a patient without over-pressurizing the patient's lungs.

Another object of the present invention is to provide a ventilator which does not cause detrimental changes to the compliance of the alveolar sacs.

A further object of the present invention is to provide a sufficient volume of air exchange, combined with enhanced molecular diffusion of the gases in the lungs to support the full oxygenation and ventilation of a patient.

A still further object of the present invention is to provide mucociliary clearance to remove fluid and mucus from the lungs.

Another object of the present invention is to allow the patient to sigh periodically and fully reinflate the alveolar sacs.

Another object of the present invention is to provide a driver for a high frequency oscillating ventilator capable of operating at high power levels without overheating.

Another object of the present invention is to provide a high frequency oscillating ventilator which operates at low mean airway pressures, thereby reducing the danger of lung damage due to barotrauma.

Another object of the present invention is to provide a 'ventilator which combines high frequency ventilation and low mean airway pressure, thereby facilitating surgical procedures, especially in the chest cavity and head, due to the fact that intracranial pressure is reduced and there is almost no movement of the lungs or chest cavity.

Another object of the present invention is to provide a high - frequency oscillating ventilator which is capable of accurately translating a polarized electrical signal having a selected period, frequency and amplitude into a polarized pressure wave in a gas A further object of the present invention is to provide a high frequency, oscillating ventilator in which the period, the frequency, and the amplitude of the pressure wave produced by the driver can be varied according to the conditions required for the use of the ventilator.

Another object of the present invention is to provide a high frequency, oscillating ventilator which produces a polar square wave in the flow of gas delivered to the air-breathing patient.

Another object of the present invention is to provide a high frequency, oscillating ventilator in which the inspiration to expiration ratio can be selectively varied according to the particular conditions under which the ventilator is being used.

A further object of the present invention is to provide a driver for a high frequency oscillating ventilator in which a single source of gas is used to both cool the driver and provide respiratory gases for a patient being maintained on the ventilator.

Another object of the present invention is to provide a high frequency oscillating ventilator using low airway pressures and . tidal volumes much smaller than the patient's dead space volume to ventilate the patient.

Another object of the present invention is to provide a high frequency oscillating ventilator which may be used to administer anesthesia and which, at the end of a surgical procedure, will provide rapid washout, and therefore, rapid recovery of the anesthesized patient.

Another object of the present invention is to provide a double lumen endotracheal tube for use with the high frequency oscillating ventilator of the present invention.

These objectives, and others which will be clear to those skilled in the art who have the benefit of this disclosure, are accomplished by providing a high frequency oscillating ventilator comprising a source of gas, a housing including a magnet and a diaphragmatically sealed piston mounted therein, and means ' conducting the flow of gas from the gas source to the space within the housing on the first side of the piston. A coil is mounted to the first side of the piston. Means is provided in the housing to direct the flow of gas delivered by the gas source to the first side of the piston, around the coil and through the housing to the atmosphere, thereby cooling the coil. Means is provided to connect the gas source, the space within the housing on the second side of the piston and the airway of a patient, as is a means for reversing the polarity of the current flow in the coil, thereby causing the coil to move back and forth within the housing relative to the magnet. The back and forth movement of the coil produces a polarized pressure wave in the flow of gas in the connecting means due to the connection between the coil and the piston.

The present invention is also directed to a driver for a high frequency oscillating ventilator comprising a housing including a magnet and having a diaphragmatically sealed piston therein, means in the housing operable to connect the space in the housing on the first side of the piston to a flow of gas, and a coil mounted to the first side of the piston. Also provided is a means in the housing operable to direct the flow of gas delivered to the first side of the piston around the coil and through the housing to the atmosphere, thereby cooling the coil. The space within the housing on the second side of the piston, the airway of the patient and the flow of gas are connected by a connecting means, and means is provided which is operable to reverse the polarity of the current flow in the coil, thereby causing the coil to move back and forth in the housing relative to the magnet to produce a polarized pressure wave in the flow of gas in the connecting means.

The present invention is also directed to a method of ventilating a patient comprising simultaneously delivering a flow of gas to both the first and second sides of a diaphragmatically sealed piston mounted in a driver, and directing the flow of gas delivered to the first side of the piston through a means for moving the piston back and forth within the driver, thereby cooling the driver. The piston is moved back and forth within the driver over a predetermined distance, thereby creating a polar pressure wave in the flow of gas delivered to the second side of the piston. The flow of gas delivered to the second side of the piston is directed into the lungs of an patient, and that flow of gas is then directed out of the lungs of the patient to the atmosphere. The method may additionally comprise the equalization of the pressures on both sides of the piston.

The present invention is also directed to a double lumen endotracheal tube for use in connection with the high frequency oscillating ventilator described herein comprising an elongate first tube having a fitting on one end thereof for connection to a high frequency oscillating ventilator and a concentric, elongate second tube running parallel to the first tube along a . portion of the length of the first tube. The integral second tube diverges from the first tube at a point along the length of the first tube which will allow the insertion of the concentric first and second tubes into the airway of a patient such that the second tube diverges from the first tube at a point outside the patient when inserted into the patient's airway. An inflatable cuff operable to effect a relatively air-tight seal between the concentric first and second tubes and the patient's airway is mounted to the integral tubes at a suitable location along their length.

DETAILED DESCRIPTION OF THE INVENTION

As used throughout this specification, the term "patient" will be used to refer to both human patients and other air breathing animal patients.

The preferred embodiment of the invention is a ventilator which uses a signal generator which produces a variable frequency, variable period square wave signal. The signal is directed through an amplifier which has a variable power output. A polar converter converts the square wave to a polar square wave. The amplifier drives a bidirectional linear motor which is connected to a diaphragm which supplies energy to gas in the ventilator. Due to the bidirectional motor, the pressure wave produced has a first portion with a positive slope and a second portion with a negative slope. This causes respirating gas to be both moved into the subject's airway and withdrawn from the subject's airway. Due to the fact that the square wave is polar, the diaphragm produces a positive and negative pressure in each cycle, relative to the static airway pressure of the patient.

Figure 1:
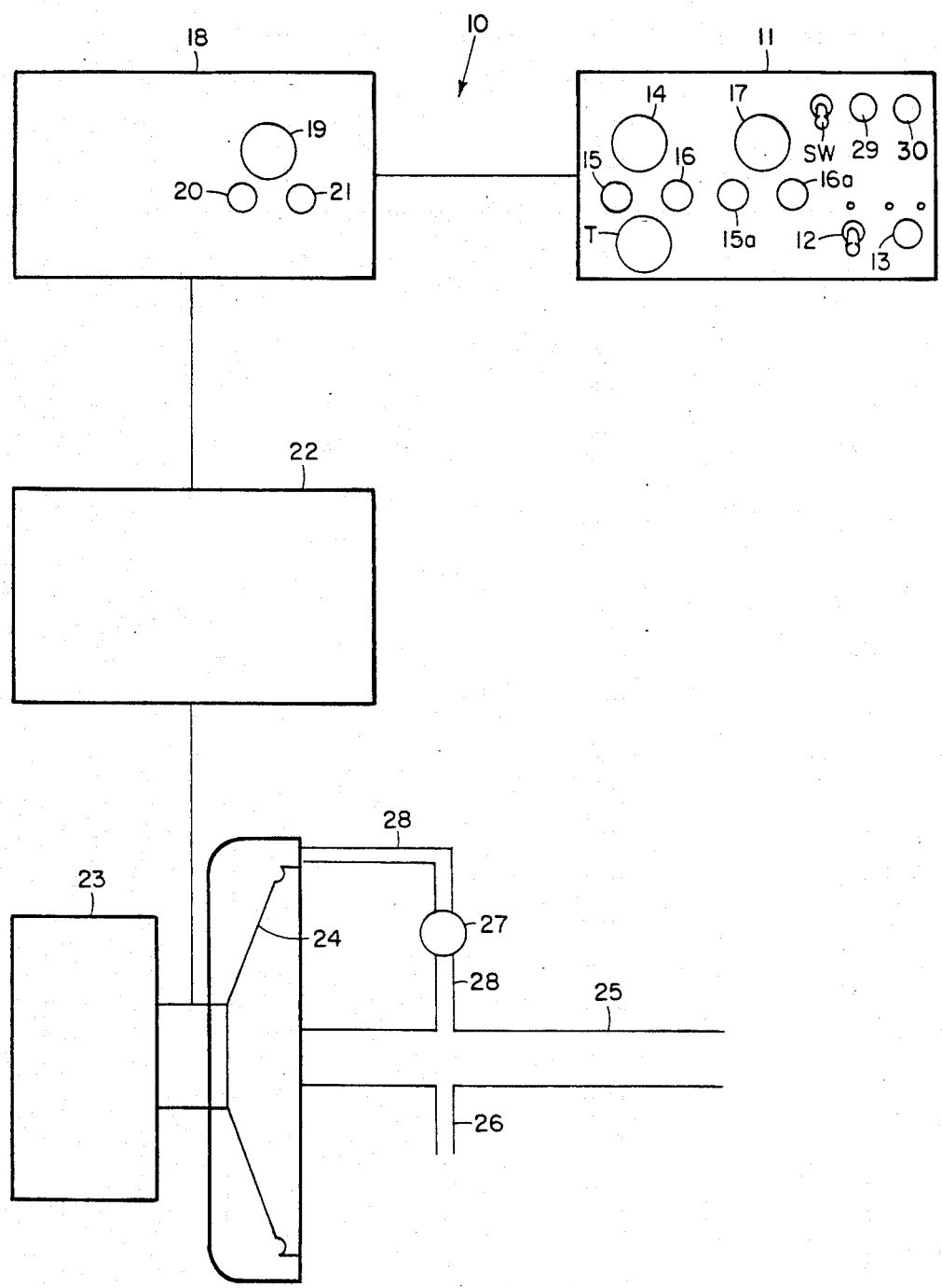
FIG. 1 is a schematic diagram of a high frequency oscillating ventilator constructed according to the present invention.

Referring to FIG. 1 of the drawings, there is shown a schematic view of a high frequency oscillator 10 constructed according to the present invention. The high frequency oscillator 10 includes a signal generator 11. When the switch 12 is turned on, an hour meter T begins running and the signal generator begins operation. Control knob 13 selects one of the two channels which may be alternately selected. A meter 14 indicates the frequency of the signal generated for the selected channel. The control knobs 15 and 16 set the frequency for the first and second channels respectively. The control knobs 15a and 16a control the I:E ratio for the respective first and second channels. A meter 17 indicates the period of the square wave signal generated, expressed as percent inspiration, which coincides with the inspiration to expiration ratio or the I:E ratio. The apparatus is capable of varying the I:E ratio from about 80:20 to 20:80, a range useful in achieving desired waveforms during clinical applications of the machine. The I:E ratio is the duration of the inspiration or positive period of the cycle over the expiration or negative period of the cycle.

A mixer-timer is controlled by switch SW and control knobs 29 and 30. When the switch SW is on and the control knob 13 is set on channel one, the setting of the knob 29 provides a predetermined first period of time to elapse during which the system operates on channel one. At the end of the first predetermined period of time, the mixer-timer causes the machine to change to channel two for a second predetermined period of time as set by control knob 30. After the second predetermined period of time has elapsed, the machine reverts to operation on channel one for the first predetermined period of time. The machine continues cycling between channels one and two when switch SW is in the on position.

The signal produced by the signal generator is a variable frequency, variable period square wave. This signal is directed to an amplifier 18 which is connected to the signal generator. High frequency ventilation is considered to be any form of ventilation with a frequency that is approximately two times or more greater than the patient's resting respiratory frequency. The output of the amplifier 18 is shown on the meter 19 and the power gain is adjusted by control knobs 20 and 21 which control the first and second channels, respectively. The signal generated by the amplifier is a variable power, variable frequency and variable period square wave.

The signal from the amplifier 18 passes to a polar converter 22 which is connected with the amplifier. The polar converter 22 serves the dual function of polarizing the square wave and providing a connection between the power supply and a linear motor 23. Linear motor 23 drives a piston 102 (see FIGS. 6 and 7) connected to a diaphragm 24 (shown schematically as a single line in FIG. 1; as noted below in connection with the discussion of FIGS. 6 and 7, the diaphragm 24 is actually comprised of two halves 100 and 101) which converts mechanical motion to pressure ' waves in gas. Piston 102 transmits energy to the gas in connecting means, or tube 25. In a preferred embodiment, line 28 is provided as a means of connecting the space on one side of - piston 102 to tube 25, thereby equalizing the pressures on both sides of piston 102. Valve 27 may be provided in line 28 to further the object of equalizing pressures on both sides of piston 102, as will be discussed. Line 26 provides a gas conducting means connecting tube 25 with a source of gas (not shown) Tube 25 connects the line 26 and the column of air on the first side of piston 102 to the lungs of a patient (also not shown) The valve 27 allows pressure on both the second and second sides of the piston 102 to equalize to the mean airway pressure in tube 25. A change in mean airway pressure is believed to not affect the waveform because of the equalization. The mean airway pressure (MAP) is the average pressure in the airways of a patient. A line with a valve in it (not shown in FIG. 1; see FIG. 9, in which the line is assigned reference numeral 76 and the valve is given the number 78) is provided through which gas leaves the patient's lungs. The valve 78 (see FIG. 9) is capable of varying mean airway pressure from about 3 to about 140 cm H2O, the upper limit being imposed by the pressure at which the lungs may be damaged. Generally, the valve will be set in the range of from about 3 to about 30 cm H2O.

Figure 2:
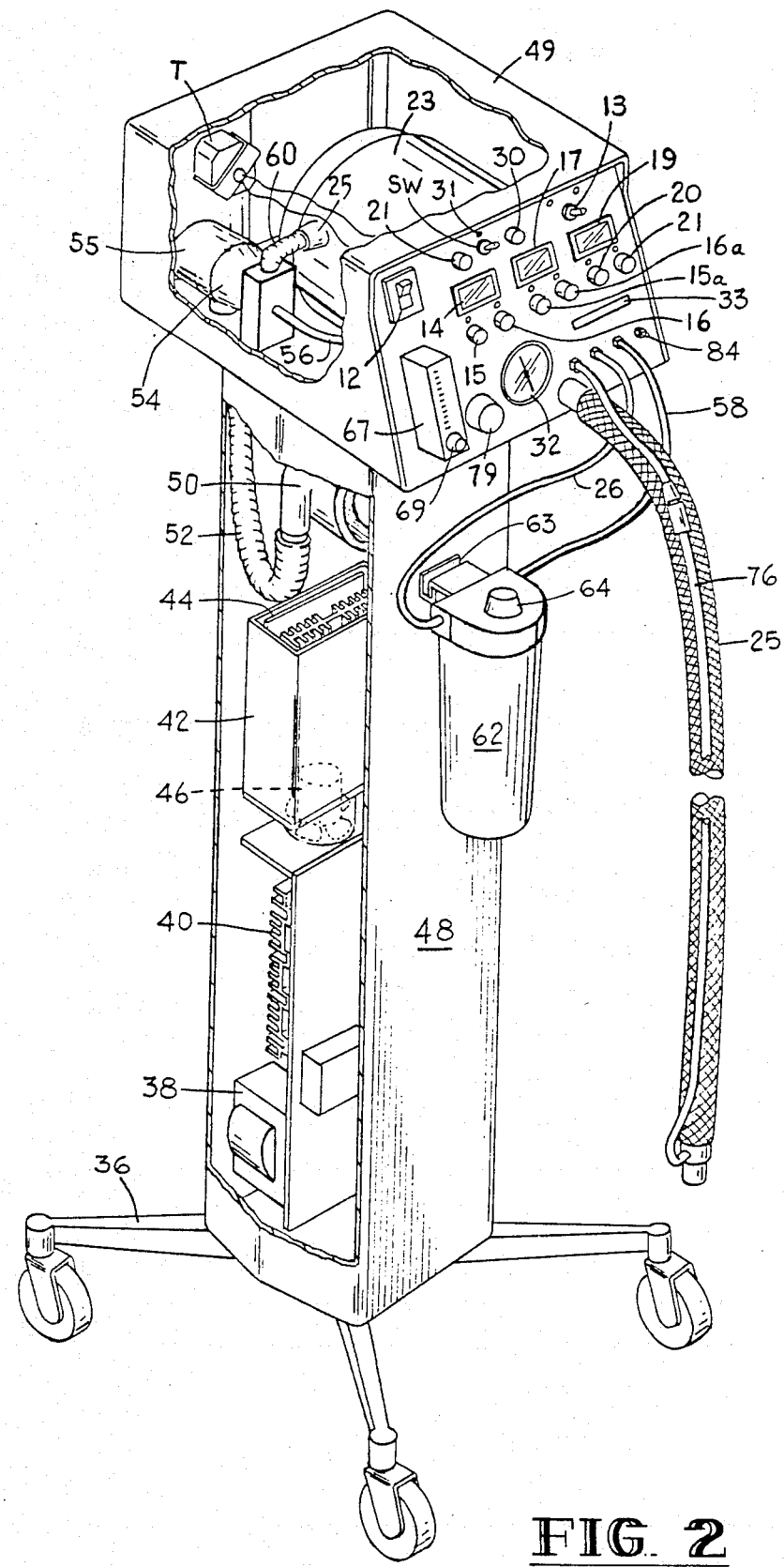
FIG. 2 is a perspective view of a high frequency oscillating ventilator constructed according to the present invention.
Figure 3:
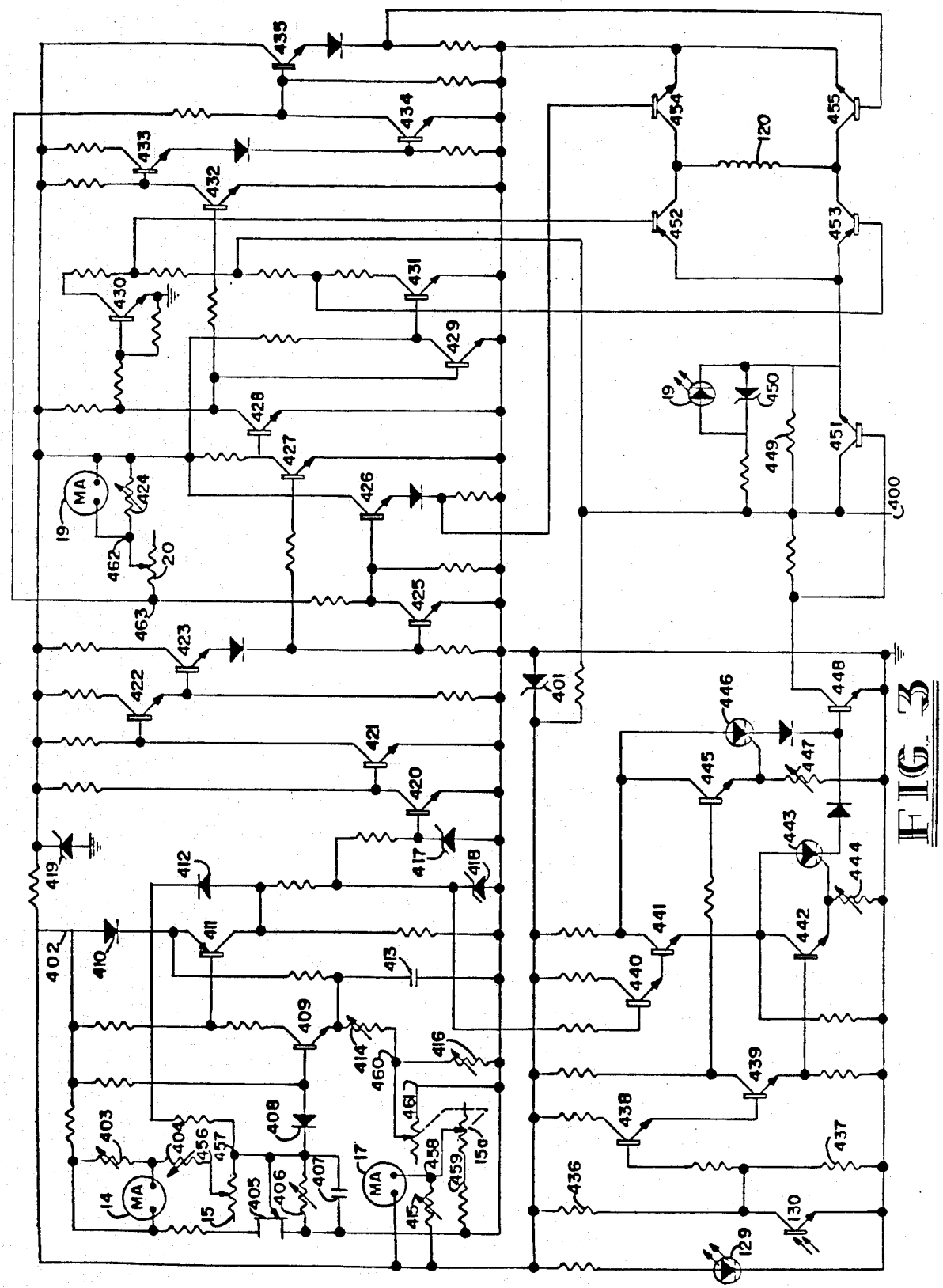
FIG. 3 is a schematic circuit diagram showing a portion of the electrical circuitry used in the apparatus of FIGS. 1 and 2.
Figure 5:
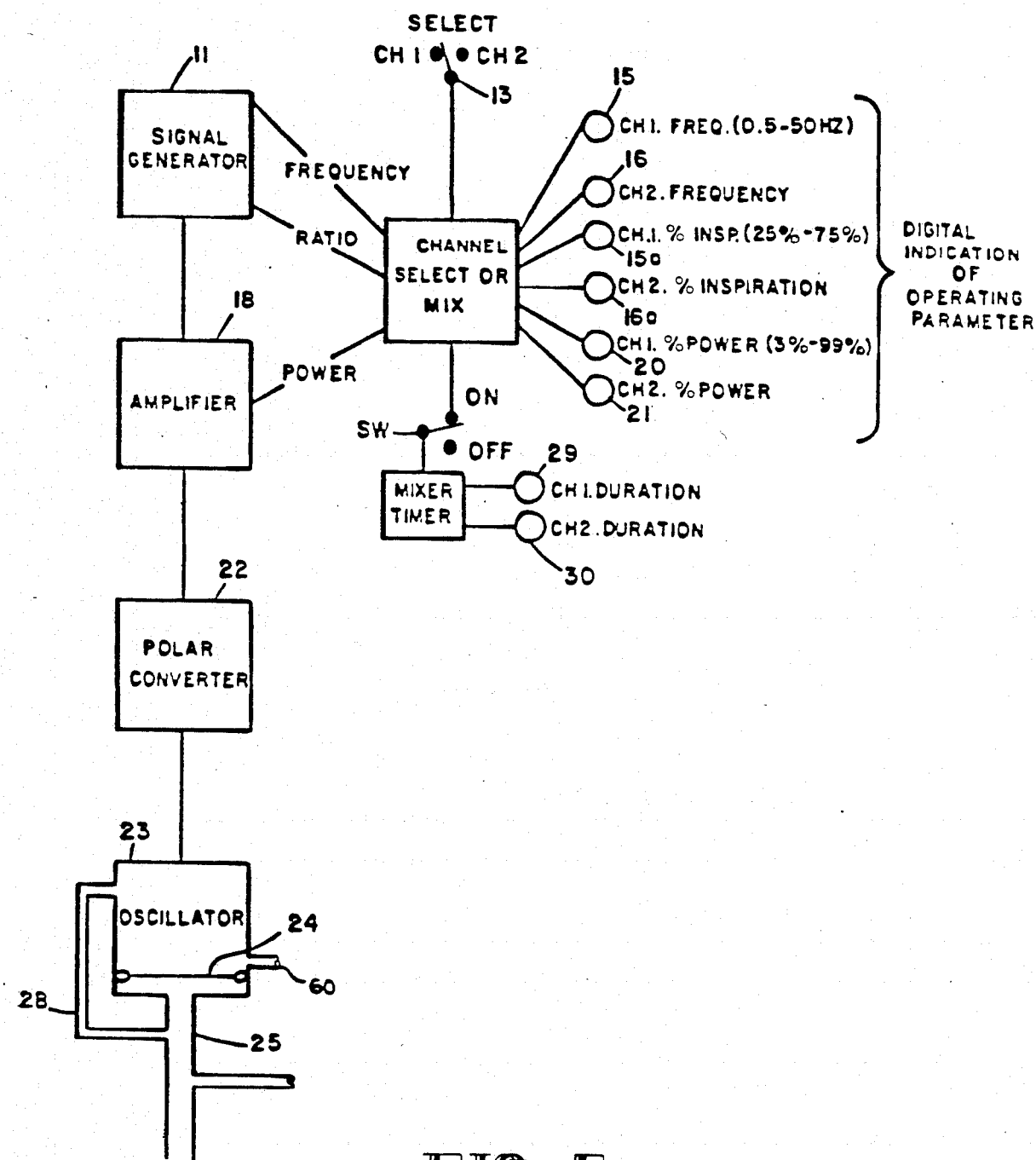
FIG. 5 is a block diagram of the embodiment of the invention shown in FIGS. 1 and 2.

Referring to FIG. 2 of the drawings, there is shown a perspective view of a high frequency oscillator 10. The high frequency oscillator 10 includes a signal generator and polar converter (not numbered) as shown in FIGS. 1, 3 and 5. When the switch 12 mounted in control panel 35 is moved to the on position, power is supplied to the signal generator 11 as shown in FIG. 3. Control knob 13 selects one of two channels which may be alternately selected. Meter 14 provides a digital readout of the frequency as a signal is generated for the selected channel. The control knobs 15 and 16 set the frequency for the respective first and second channels. They are adjustable from about 5 Hz (300 cycles per minute) up to about 50 Hz (3000 cycles per minute).

The control knobs 15a and 16a set the period for the respective first and second channels to control the I:E ratio for the respective first and second channels. The digital meter 17 shows the period of the polar pressure wave as the inspiration to expiration ratio or the I:E ratio.

Channel 1 on the apparatus is selected by moving the switch 13 to the "1" position which will light up the yellow LED's (not numbered) above the appropriate control for adjusting channel 1 operation. Similarly, channel 2 may be selected by switching the channel selector switch 13 to the "2" position which will light up the appropriate yellow LED's (not numbered) mounted to control panel 35 above the respective controls for adjusting channel 2 operation. When channel selection is made, there is a one second delay before power is applied to the alternate channel. This delay is also present when switch 12 is switched to the on position.

The present inspiration can be increased by clockwise rotation of the control knobs 15a and 16a, which engages the I:E ratio. Clockwise rotation of the channel 1 control knob 15a lengthens the period of time the piston 102 (see FIGS. 6 and 7) spends o the positive side of the high frequency stroke in channel 1. Similarly, clockwise rotation of the channel 2 control knob 16a lengthens the period of time the piston 102 (see FIGS. 6 and 7) spends on the positive side of the high frequency stroke in channel 2. The LED indicators (not numbered) mounted in control panel 35 above the appropriate controls for the control knobs 152 and 162 indicate the channel which is being activated.

The output of the amplifier is shown on digital meter 19 and the amplitude of the pressure wave produced by the driver is adjusted by control knobs 20 and 21. LED indicators (not numbered) mounted in control panel 35 above the appropriate control knobs 20 and 21 light up to show which channel is being used. Clockwise rotation of the channel 1 power control knob 20 increases the amount of power applied to the high frequency driver shown in FIGS. 6 and 7. Similarly, clockwise rotation of the channel 2 control knob 21 increase the amount of power applied to the high frequency driver. Turning the channel 1 control knob 15 clockwise increase the ventilator cycle rate if the channel selector is in the "1" position. Similarly turning the channel 2 control knob 16 clockwise increase the ventilator cycle rate if the channel selector is in the "2" position.

Control of the mixer-timer is provided by mixer switch SW and control knobs 29 and 30. By turning knobs 29 and 30 clock wise, the duration on channel 1 can be increased to up to 30 minutes and the duration on channel 2 can be increased to up to 3 minutes. An LED indicator 31 indicates when the switch SW is in the on position An airway pressure gauge 32 is mounted in control panel 35 to monitor breathing circuit pressure. A fuse or circuit breaker (not numbered) protects the entire machine. LED bar 33 is provided to give a continuous visual indication of piston activity, as will be explained. The ports 37, 39 and 41 in control panel 35 are provided for attachment of line 58, line 26, and line 76, respectively. Discharge port 84 is also mounted in control panel 35.

High frequency oscillating ventilator 10 is built on a chassis 34 which is mounted on wheeled dolly 36. A transformer/power pack 38, including heat sink 40, is mounted to chassis 34 at the bottom thereof. Circuit board holder 42 is mounted to chassis 34 above heat sink 40, and contains the printed circuit boards, designated generally at 44. A cooling fan 46 is provided to blow a stream of cooling air through circuit board holder 42. Blower 50 [is mounted above circuit board holder 42 and directly below linear motor 23. Removable front and back covers, designated generally at 48 and shown in cutaway view in FIG. 2, are provided to cover chassis 34 and the various components mounted thereon, and cover 49 is provided to encase the linear motor 23 and the workings mounted to control panel 35. Mount 63 is provided on cover 48 for attachment of a device 62 for conditioning the respirating gas such as a humidifier, vaporizer or nebulizer for adding agents to the respirating gas.

Referring to FIG. 5 of the drawings, which schematically shows the circuitry of the high frequency oscillating ventilator 10, there is shown a signal generator 11 having a frequency range of about 30-3000 cycles per minute (i.e., about 0.5 Hz up to 50 Hz) The frequency on channels 1 and 2 is about 0.5-50 Hz. The percent power range for channels 1 and 2 is about 3%-99%, and increasing the percent power increases the amount of gas which is forced into and pulled back out of the patient during each cycle of back and forth movement by diaphragm 24. Since increases in the frequency enhance the rate of diffusion of the gases, thereby facilitating respiration, embodiments of the present invention have been constructed which are capable of operating at frequencies which are considerably higher than 50 Hz. Adjustment of potentiometer 404 (see FIG. 3) allows the operation of the high frequency oscillating ventilator 10 at frequencies in excess of 200 Hz.

The signal produced by the signal generator 11 shown in FIG. 5 is a constant voltage, variable frequency, variable period square wave. This signal passes to an amplifier 18 connected to the signal generator 11. As discussed above, the power gain for channels one and two is adjusted by control knobs 20 and 21, respectively. The signal generated by the amplifier 18 is directed to a polar converter 22 which is connected to amplifier 18. The polar converter 22 serves a dual function of polarizing the square wave and providing the connection between the power supply and the linear motor or oscillator 23. The linear motor 23 includes a piston 102 connected to a diaphragm 24 (as noted above, diaphragm 24 is comprised of two halves; see FIGS. 6 and 7) which converts mechanical motion to pressure waves in the gas.

Figure 8A:
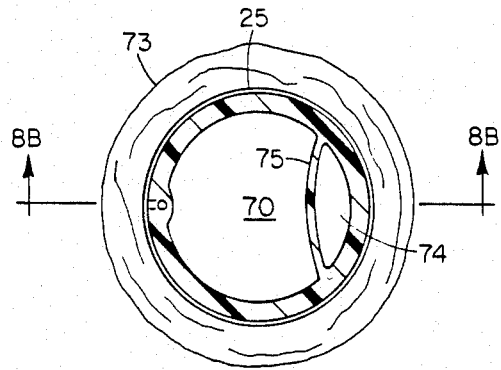
FIG. 8A is a cross-sectional view of the endotracheal tube of FIG. 8B taken at the line 8A—8A in FIG. 8B.

Oxygen or compressed gas is added to the system through line 26 which is connected to connecting means, or tube 25. The line 28 allows pressure on both the first and second sides of the piston 102 to equalize to the mean airway pressure in tube 25. The tube 25 is connected to endotracheal tube 68 (see FIGS. 8 and 9) to provide breathing function.

Figure 4:
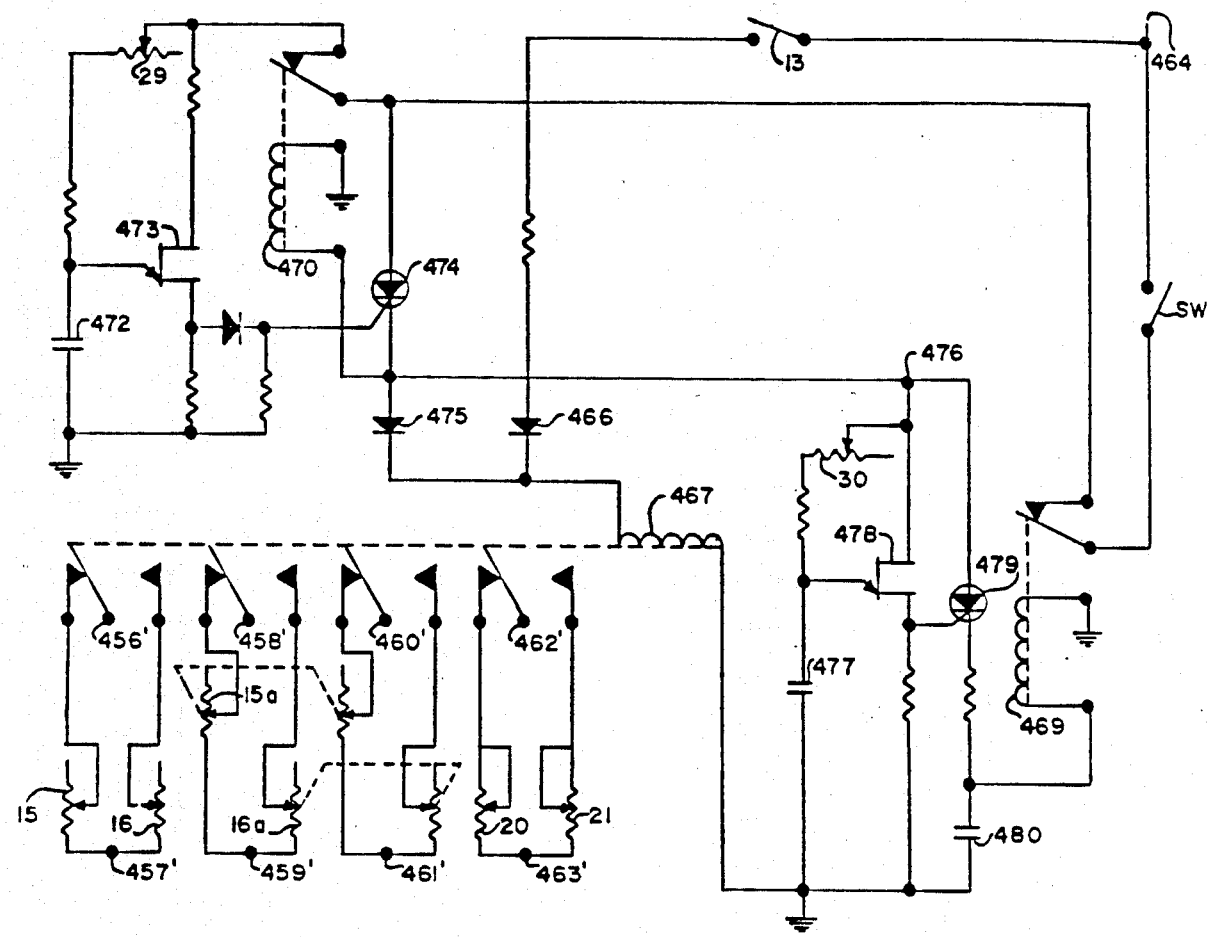
FIG. 4 is a schematic circuit diagram for providing two independent sets of operating parameters for two channel operation of the apparatus of FIGS. 1, 2 and 3.

The circuits in the system of FIG. 5 can be realized by use of diagrams similar to those of FIGS. 3 and 4, as would be apparent to one of ordinary skill in the art.

In operation, channel 1 of the signal generator 11 is set to produce a frequency of approximately 3 Hz or greater. The desired I:E ratio is set and a source of pressurized gas is attached to line 52. Respirating gas is delivered through lines 58 and 26 at a flow rate (called a "bias flow") of, for instance, approximately 5 liters per minute. The valve 78 in return line 76 (see FIG. 9) is set so that the static pressure in line 25 is relatively low yet sufficient to hold the patient's lungs in a partially inflated condition. The system is operated in this condition to fully respirate the patient. ' During the operation of channel 1, bias flow is supplied at a rate of from about 2 to about 20 liters per minute into line 25 and gases from return line 76 (see FIG. 9) exit from the patient's lungs at the same rate. However, because the concentration of oxygen in line 25 is greater than the concentration of oxygen in the gas containing diffused carbon dioxide from the patient, the oxygen is diffused into the subject's lungs. The diffusion acts with a volume exchange effect produced by the bidirectional drive of linear motor 23 to cause gas exchange in the lungs. Although the mechanism for causing complete gas exchange is not completely understood, it is believed to be a combination of enhanced molecular diffusion, asympathetic vibrations of the lung tissue and volume exchange.

It is believed that enhanced molecular diffusion is greatly responsible for the gas exchange. This diffusion is enhanced by the vibrational energy added through the reciprocation of piston 102, which is connected to diaphragm 24, to the point where much of the oxygen in the respirating gas reaches the patient's lungs and replaces the carbon dioxide therein. This gas exchange can be more clearly envisioned by viewing the source of gas from line 26, as supplying, for example, oxygenated air which produces an oxygen gradient throughout the bias flow with a higher partial pressure of oxygen existing at the outlet of line 28 than in the rest of the system. The patient's lungs can be viewed as a source of carbon dioxide which produces a $CO_2$ pressure gradient throughout the bias flow. The partial pressure of the $CO_2$ is greater in the lungs than in the rest of the system. What the ventilator of the present invention does is to promote the diffusion of these gases throughout the bias flow, line 25 and lungs of the patient to such an extent that a large portion of the oxygen reaches the alveolar sacs of the patient. It should also be understood that the static pressure produced by valve 78 (see FIG. 9) is also present to hold the air passages open, thereby ensuring that diffusion can take place. This is to be clearly contrasted with the presently known volume ventilators which use high pressure gas to actually inflate the subject's lungs to produce only a volume exchange whereby oxygenated gas is forced under pressure into the lungs to expand the lungs during inspiration and the compliance of the lungs forces the carbon dioxide out during expiration. These known ventilators produce a volume exchange of gas analogous to the normal breathing function.

The asympathetic vibrations applied to the patient's lungs appear to promote mixing of the gases deep in the lungs and therefore also enhance gas exchange. These vibrations also appear to aid in moving gases into and out of the lungs.

This type of gas exchange is to be contrasted with known high frequency jet ventilators which only force gas into the lungs and rely on the compliance of the lungs to push gas back out. If it were not for the natural phenomena of lung compliance occurring apart from the jet ventilator, the pressure in the patient's lungs could rise indefinitely, whereas the present invention forces the pressure in the lungs to return to a lower level by actively drawing gases back out of the lungs.

As discussed above, the signal driving linear motor 23 is driven by a polar square wave. Ideally, the pressure wave produced in tube 25 should also be square in shape, hence the line 28 and valve 27 to equalize the pressure on both the first and second sides of piston 102. Nevertheless, this pressure wave does not quite have a perfect square shape. The deviation in shape is due to the fluid flow characteristics of the tube 25 and the compressibility of the gases. In actuality, electrical waveforms are not perfectly square in shape either. Accordingly, these waveforms, which are characterized as square waves, exhibit for each cycle a relatively rapid rise, a relatively horizontal portion, a relatively rapid decline and a relatively horizontal portion. This waveform is distinguished from the high frequency sine wave oscillatory ventilator such as that described in the Emerson patent which constitutes part of the prior art. Such sine wave oscillators have been used experimentally but have not been commercially developed as far as is known. High frequency jet ventilators exhibit a sawtooth pressure wave, namely a relatively rapid rise and a relatively gradual decline to a value greater than static airway pressure.

Also as discussed above, the amplitude of the pressure wave can be varied to suit different needs. In accordance with the desirable features of maintaining a low pressure in the lungs of the patient, the pressure wave is polar; that is, has both a positive portion and a negative portion relative to the static airway pressure in the patient. In this manner, the pulse amplitude does not affect the mean airway pressure except to the extent produced by a difference in pulse width of the positive and negative portions of the pulses. Thus, the mean airway pressure is held at approximately the static pressure set by the valve 78 in return line 76 (See FIG. 9). Each electrical pulse, and hence each pressure pulse, has a positive going portion and a negative going portion. Due to the connection of line 28 of FIG. 1, the positive and negative going portions of the pressure pulse are relative to the static airway pressure and thus the static airway pressure is equal to the mean airway pressure.

As long as these positive and negative going portions are kept within reasonable limits, there is no danger of overpressurizing the lungs of the patient. It has been found that a lower peak to peak amplitude can be used as a greater static airway pressure is used. For severely damaged lungs, it may be necessary to use a static pressure as high as 40 cm $H_2O$. Care should be taken to be sure that the instantaneous pressure caused by the system in the lungs does not reach a level low enough to cause lung collapse.

The pressure of the pressure wave may vary between 5 cm $H_2O$ and 15 cm $H_2O$. That is, on the forward stroke of linear motor 23, the pressure in the patient's lungs is raised by 10 cm $H_2O$ by forcing gas into the lungs. On the rearward stroke of linear motor 23, the pressure wave is forced to fall from 15 cm $H_2O$ to 5 cm $H_2O$, thereby drawing gas out of the lungs. At the same time, the pressure wave is polar relative to the 10 cm $H_2O$ static pressure level produced by setting the valve 78 (See FIG. 9). Thus, the mean airway pressure is maintained at approximately 10 cm $H_2O$ The peak to peak amplitude (power) of the pressure wave can be varied without affecting the patient's mean airway pressure. Likewise, the patient's mean airway pressure can be set independently of the pressure wave amplitude by adjusting the static pressure f the ventilation to the desired mean pressure value.

As should be clear from the foregoing example, the bias flow of the gas into line 26 should be maintained at a substantially constant rate since this bias flow provides the source of fresh respirating gas and also acts with the valve 78 in return line 76 (see FIG. 9) to maintain the static pressure.

Channel two of the ventilator can be set at a second amplitude. When the control switches to channel two under the influence of the above-described timing and switching circuitry, the ' high frequency oscillating ventilator 10 operates at the levels " set for that channel for the period of time selected by control knob 30. The second channel is useful for providing a second high frequency signal which can be alternated with the first high frequency signal. Different high frequencies may be beneficial to produce different results. For example, one frequency may be found to be beneficial for the removal of mucus from the patient's lungs and airways while a second frequency may produce more efficient air exchange. Accordingly, by providing the ventilator with the ability to automatically switch between two frequencies, power levels and I:E ratios, the desired results can be achieved most efficiently.

It has been suggested by researchers using high frequency ventilators that after a patient has been managed on a high frequency ventilator for long periods of time, the lungs should be exercised, or "sighed" occasionally. A simple method of "sighing" with the apparatus of the present invention is to occlude the port 84 of discharge tube 80 until mean airway pressure rises by about 5 to 10 cm $H_2O$ and then releasing it. Discharge tube 80 may also be provided with a solenoid valve (not shown) which periodically closes the discharge tube 80 under the 1 control of a timer (not shown) for a predetermined period of - time, the time the valve is closed being selected by determining the period of time the valve should be closed to raise the airway pressure by about 5 to 10 cm $H_2O$.

The electrical circuitry of the ventilator will now be discussed in detail with reference to FIG. 3, which shows the ventilator with only one signal generating channel for simplicity.

In FIG. 3, a positive DC voltage is shown applied to the circuit at point 400. A zener diode and resistor at point 401 reduce the voltage at 15V. The signal generator 11 (see FIG. 1) section of the schematic begins at point 402. Milliammeter 14 measures the current flowing to the emitter of uninjunction transistor 405. Variable resistor 403 is adjusted to cause milliammeter 14 to indicate the frequency of the signal. Variable resistor 404 is adjusted to limit the maximum frequency of the circuit Potentiometer/control knob 15 allows the operator to select any frequency between the minimum and the maximum. Variable resistor 406 is adjusted to bleed the emitter leakage current of unijunction transistor 405 which prevents capacitor 407 from being charged except through potentiometer 15.

As capacitor 407 is charged, the voltage at the emitter of unijunction transistor 405 rises until it reaches a fixed proportion of the differential between base 1 and base 2 of the unijunction transistor 405 at which time it conducts, which discharges capacitor 407 and causes diode 408 to become forward biased. The signal at the cathode of diode 408 is a sawtooth wave typical of an a stable unijunction relaxation oscillator and its frequency is variable through potentiometer 15.

As diode 408 becomes forward biased due to the negative resistance effect of unijunction transistor 405, it causes transistor 409 to turn off, which in turn causes transistor 411 to turn off. As the base of transistor 409 becomes positive again, it begins to conduct and transistor 411 turns on after a period of time determined by potentiometer 15a. Capacitor 413 drives transistor 411 into saturation and it remains on until unijunction. transistor 405 again conducts which provides the positive portion of the square wave. Diodes 410 and 412 add to the stability of the circuit by providing a base bias voltage differential to transistor 411 and feedback to the emitter of unijunction transistor 405. Variable resistors 414, 415 and 416 with milliammeter 17 and potentiometer 15 comprise the means whereby the square wave signal is made a variable period square wave and of indicating its condition of variability as percent inspiration on milliammeter 17. When the resistance of potentiometer 15a is at the minimum, the current through milliammeter 17 is at the maximum, indicating a high inspiration percent, and the charging time of capacitor 413 is at the maximum. Variable resistor 415 is a shunt for milliammeter 17 which allows it to be calibrated to indicate the exact percent of inspiration of the invention. Variable resistor 414 sets the maximum inspiration percentage and variable resistor 416 allows calibration of potentiometer 15a.

Zener diodes 417 and 418 condition the variable frequency, variable period square wave to one of constant amplitude. Without them, the positive amplitude of the square wave varies with the duty cycle. The zener diode and resistor at point 419 reduce the voltage to the amplifier section to 5V. Transistors 420, 421, 422 and 423 comprise a means whereby the low power signal at the base of transistor 420 is amplified.

Transistors 452, 453, 454, and 455 comprise the driving transistors of the polar converter which apply a bipolar signal to coil 120 of the linear motor 23 (see FIGS. 6 and 7) which produces the pressure variations in the gas in the ventilator as will be explained. When transistors 452 and 455 are on while transistors 453 and 454 are off, current flows through coil 120 in one direction. Transistors 452 and 453 are used in a switching mode and are either biased off or driven into saturation. Transistors 454 and 455 are used in the transient regions and are biased off, but the extent to which they are turned on is determined by potentiometer/control knob 20.

When transistor 423 is on, transistor 425 is on and transistor 426 is off, thereby biasing transistor 454 off. Transistor 427 is on, transistor 428 is off, transistor 429 is on and transistor 431 is off, thereby biasing transistor 453 off. Simultaneously, transistor 430 is on, transistor 433 is off, transistor 434 is off and transistor 435 is biased on to the degree allowed by the current flowing through potentiometer 20. . Transistor 455 is thereby biased on relative to the position of potentiometer 20.

When transistor 423 is off, transistor 425 is off and transistor 426 is biased on to the degree allowed by potentiometer 20 and consequently transistor 454 is biased on proportionally to the setting of potentiometer 20. Transistor 427 is off, transistor 428 is on, transistor 429 is off and transistor 431 is on thereby biasing transistor 453 on. Simultaneously, transistor 430 is off which biases transistor 452 off. Transistor 432 is off, transistor 433 is on, transistor 434 is on and transistor 435 is off which biases transistor 455 off.

Milliammeter 19 indicates the relative percent of power applied to coil 120 and is calibrated by variable resistor 424.

The remaining circuitry of FIG. 3 is to prevent mechanical contact between moving and stationary masses. An infrared light emitting diode 129 is mounted to the pole piece 135 and directed at retaining ring piston flange 103 (see FIGS. 6 and 7). Mounted next to the diode 129 is an infrared transistor 130. As the line of sight distance changes between diode 129 and transistor 130 due to the movement of piston 102 (see FIGS. 6 and 7), the voltage at the base of transistor 438 varies. Resistors 436 and 437 provide a voltage divider with an effective variable resistance through transistor 130. Transistor 438 amplifies and inverts the signal at the collector of transistor 130. Transistor 440 is driven by the square wave signal present at the anode of zener diode 418 which is amplified by transistor 441. Therefore, at the anode of silicon controlled rectifier 443, there is an opposite signal to that at the anode of silicon controlled rectifier (SCR) 446.

As the current at the base of transistor 438 increases, so does the current at the base of transistor 439. As transistor 439 conducts more, transistor 445 tends to conduct less. Simultaneously, transistor 442 tends to conduct more. Variable resistor 444 determines the current through the emitter of transistor 442 necessary to turn on silicon controlled rectifier 443. The polarity of the coil 120 is maintained in phase with the signal at zener diode 418 to cause the anode of SCR 443 to be positive when the current at the base of transistor 438 is increasing due to the movement of coil 120. When SCR 443 is turned on, it turns on transistor 448 which turns off transistor 451 which reduces the amount of current available to coil 120 by shunting it through resistor 449, thereby limiting the travel of coil 120. When the signal at zener diode 418 reverses, the voltage at the anode of SCR 443 falls below its minimum conduction limits which turns it off and consequently transistor 448 goes off and transistor 451 turns back on allowing full power to the coil 120. When transistor 451 is off, light emitting diode 129 is on and it is protected by zener diode 450.

As the current at the base of transistor 438 decreases, transistor 439 tends to conduct less, causing a greater current at the base of transistor 445. Variable resistor 447 controls the point at which SCR 446 turns on. Being in phase, as transistor 445 turns on, the voltage at the anode of SCR 446 is positive and its operation similar to SCR 443.

FIG. 4 is an electronic schematic diagram showing a timer ' for use in the circuit shown in FIG. 3 which produces two independent operating channels for the present invention and automatically switches back and forth between them. In FIG. 4, a ' DC voltage is applied at point 464. For the purposes of this 'disclosure, the circuit represented in FIG. 3 is changed by removing potentiometer 15 and connecting points 456 and 457 in FIG. 3 to points 456' and 457' respectively, of FIG. 4. Additionally, potentiometers 15a and 20 as shown in FIG. 3 are removed and points 458, 459, 460, 461, 462 and 463 are connected to points 458', 459', 460', 461', 462' and 463' respectively of FIG. 4.

When switch/control knob 13 is open, the contacts of relay 467 remain in their normally closed position. Potentiometer 15 therefore controls frequency, potentiometer/control knob 15a controls the period of inspiration or duty cycle and indication of it; and potentiometer/control knob 20 controls the power. When switch 13 is closed, relay 467 is energized, which causes potentiometer 15, 16a and 21 to control frequency, percent inspiration and power respectively, thereby giving a second set of independent operating parameters. Operationally, when switch 13 is open, the machine is said to be operating on "channel one". When switch 13 is closed, the machine is said to be operating on "channel two".

Automatic switching between channels one and two is accomplished by leaving switch 13 open and closing switch SW. Current then flows through the normally closed contacts of relays 469 and 470. Potentiometer 29 controls the time that capacitor 472 takes to charge. When the emitter voltage of unijunction transistor 473 reaches a fixed proportion of the voltage between its base 1 and base 2 leads, it will conduct sending a pulse to the gate of SCR 474 which turns it on. Relay 470 is energized which interrupts current to this "CHANNEL 1 DURATION" circuit. Relay 467 is also energized which causes switching to channel 2 as described ' above This first preset period of time set by potentiometer 29 is adjustable by the operation.

Current is also now applied to the "CHANNEL 2 DURATION" circuit beginning at point 476. Potentiometer/control knob 30 controls the time that capacitor 47 takes to charge. When the emitter voltage of unijunction transistor 478 reaches a fixed proportion of the voltage between its base 1 and base 2 leads, it will conduct, sending a pulse to the gate of SCR 479 which turns it on, which in turn charges capacitor 480 and energizes relay 469 which interrupts the current to SCR 474. This interruption de-energizes relays 469, 470 and 467 which resets the entire circuit This second preset period of time set by potentiometer 30 is adjustable by the operator. The machine will continue to switch back and forth between channel 1 and 2 until SW is opened or switch 13 is closed. Diodes 475 and 466 isolate the circuit functions.

Figure 9:
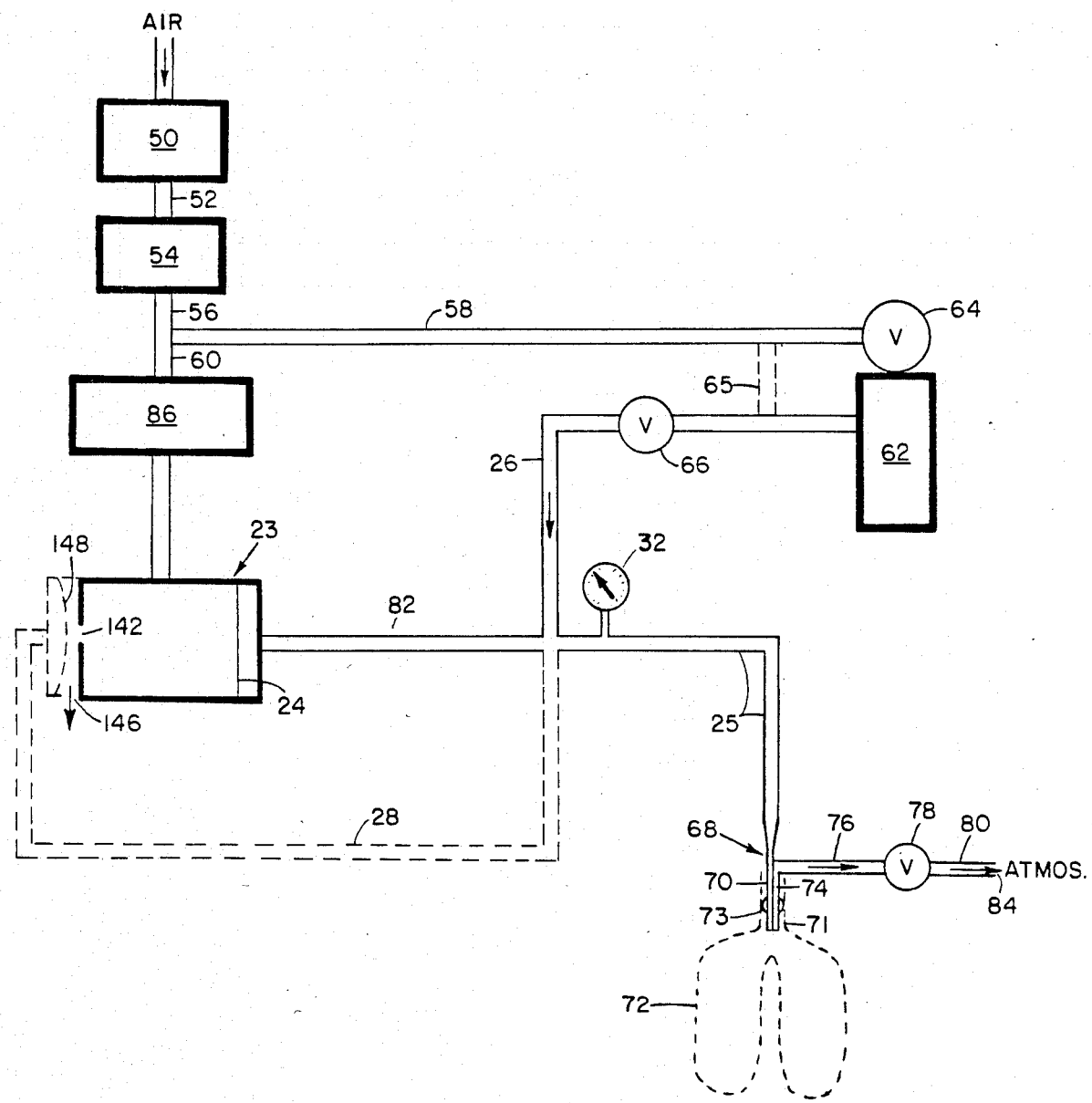
FIG. 9 is a schematic diagram of the pneumatic circuitry of the present invention.

Referring now to FIG. 9, there is shown a schematic diagram of the pneumatic circuitry of the present invention. Gas enters the ventilator through blower 50. As will be recognized by those skilled in the art who have the benefit of this disclosure, the blower 50 could be any source of gas, for instance a pressurized tank of gases of selected composition. The flow of gas produced by blower 50 is directed through line 52 to a filter 54. Filter 54 is a bacterial filter such as any of those known in the art but could also include a dust filter or any other type of filter for conditioning the air from blower 50. Filter 54 is mounted in a filter box 55 (see FIG. 2) to facilitate the removal and cleaning or changing of the filter 54. The flow of gas exits from the filter 54 into line 56, which splits into lines 58 and 60.

Proceeding along line 58, the flow of gas, now called the "bias flow", is directed to a humidifier 62, which could be a humidifier, nebulizer, vaporizer, anesthetic vaporizer, or any other means for conditioning and/or adding gases to the bias flow. The humidifier 62 will generally include a valve 64 at the inlet thereof. The humidifier or other accessory 62 is optional, and the bias flow may be directed through the line 58 to valve 66 as shown in shadow line 65, and on through return line 26 to the intersection with connecting means or tube 25. As shown in FIG. 2, valve 66 may include a manometer 67 and adjustment knob 69 to open and close line 58. The bias flow then proceeds down the tube 25 into a double lumen endotracheal tube 68, proceeding down the endotracheal tube 68 through one side 70 of the endotracheal tube 68 into the patient's lungs 72. The bias flow will then proceed back out of the patient's lungs 72 through the other side 74 of double lumen endotracheal tube 68 into return line 76, through valve 78 and on out through the port 84 in discharge tube 80 to the atmosphere.

The double lumen endotracheal tube 68 is comprised of a first tube 70 which attaches to an endotracheal tube fitting 61 and receives the bias flow from connecting means, or tube 25 at or near the patient's mouth. First tube 70 extends from the connection (not shown) with tube 25, which may be a conventional quick release connector such as is known to practicioners in the art, down into the patient's airway (shown schematically at reference numberal 71), where first tube 70 is sealed in the airway by inflatable cuff 73, as is known in the art.

A second tube 74 runs along a portion of the length of first tube 70, extending from the portion of the patient's airway below cuff 73, and out of the patient's mouth, at which point second tube 74 diverges from first tube 70 in the endotracheal tube fitting 61. During that portion of their length in which they are parallel, first and second tubes 70 and 74 are concentric, i.e., second tube 74 is contained within first tube 70 as shown in the cross-sectional view shown in FIG. 8A. The concentric first and second tubes 70 and 74 are separated by a single wall 75 as shown. The cross-sectional area of the lumen of second tube 74 should be large enough to allow the bias flow to exit the lungs without causing a significant rise in pressure. The cross-sectional area of the lumen of first tube 70 must be large enough to avoid any effect upon the pressure pulses in the bias flow set up by piston 102. In a preferred embodiment, the cross-sectional area of second tube 74 is about one third the cross-sectional area of first tube 70, however, it is expected that any ratio of cross-sectional areas of from about 1:7 up to about 1:2 would be operational. Second tube 74 diverges from the first tube 70 as return line 76 having a check valve 57 located therein and back through control panel 35 to valve 78 located therein as described above. The size of the endotracheal tube 68 has a direct effect on the amount of power required from the ventilator to achieve adequate ventilation. More power is required to ventilate a 10 pound cat through a 3.5 mm endotracheal tube than is required to ventilate a 35 pound dog through a 9.0 mm endotracheal tube. Endotracheal tubes as small as 2.5 cm may be used with small animals.

Figure 6:
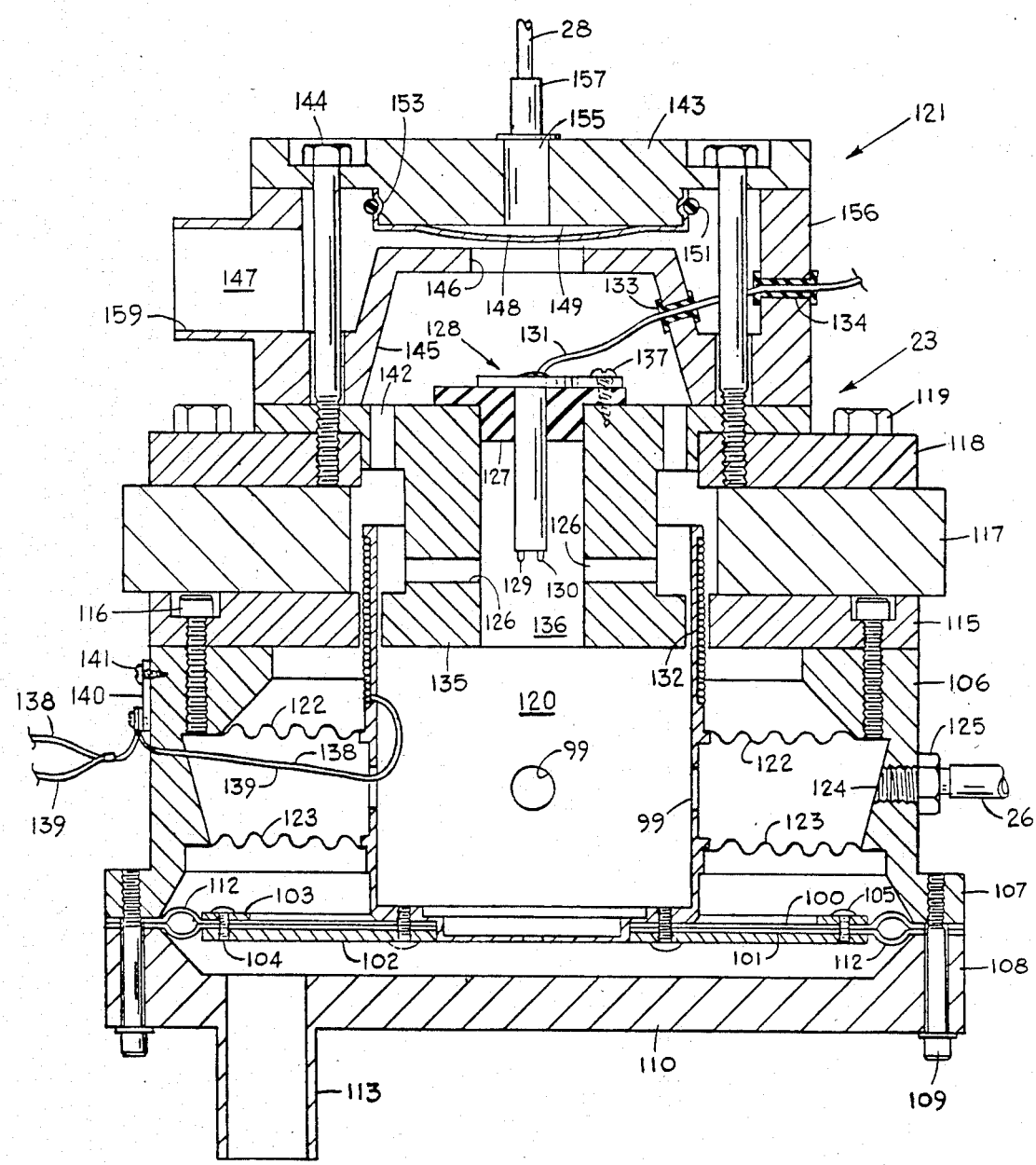
FIG. 6 is a sectional view of one embodiment of a linear motor which may be used in connection with the ventilator of the present invention.
Figure 7:
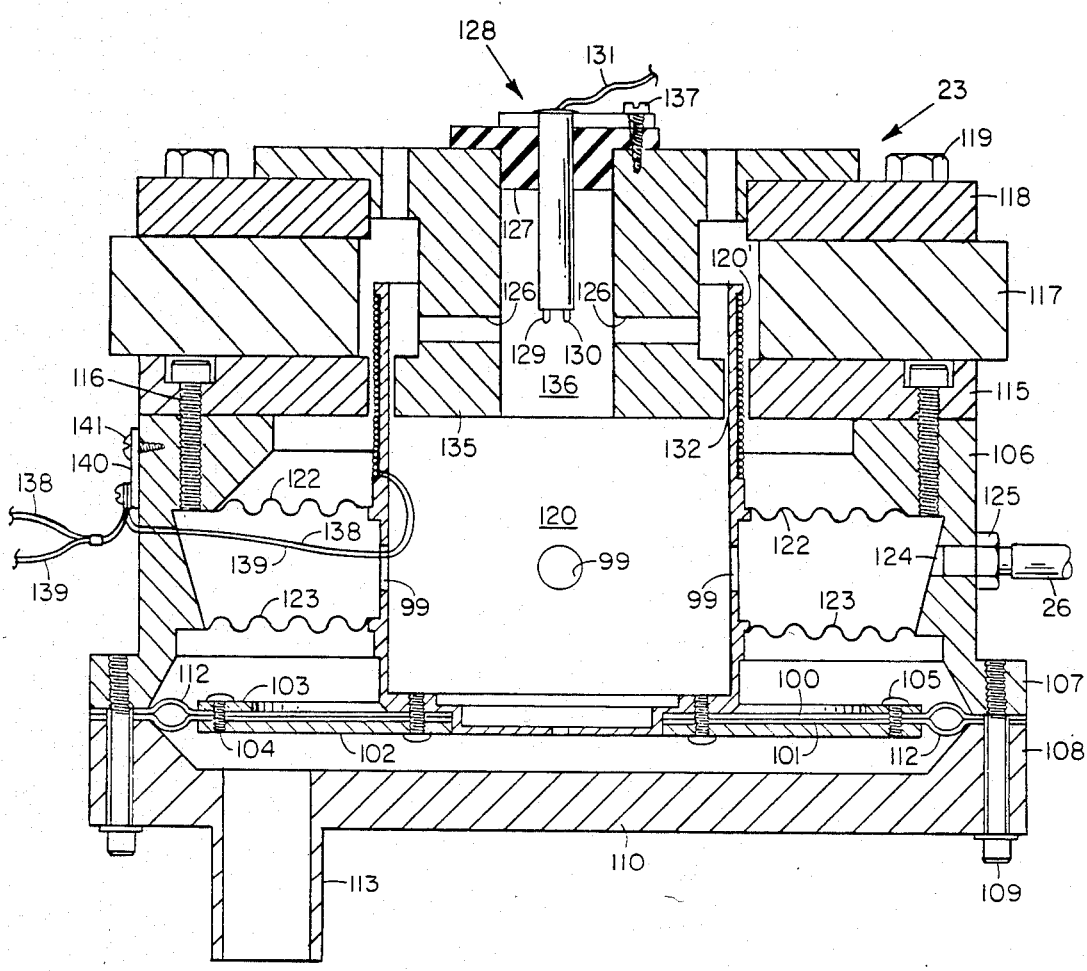
FIG. 7 is a view similar to FIG. 6 of an alternative embodiment of the linear motor of FIG. 6.

Line 82 fits onto fitting 113 on the outlet plate 110 of the high frequency oscillator 10 with the intersection of the tube 25 and line 26. An airway pressure gauge 32 is provided near that intersection to continuously monitor the pressure in tube 25. A portion of the flow of gas in line 56 is also directed from line 56 through gas conducting means, or line 60 into a pressurizing orifice 86 to the housing 106 of linear motor 23. Pressurizing orifice 86 restricts the amount of gas which pro of the flow in line 56 in order to insure the availability of an adequate bias flow even when high mean airway pressures are used. Referring now to FIGS. 6 and 7, it can be seen that the flow of gas (now referred to as the "cooling gas") is directed through the inlet 124 and into the linear motor 23 on the first side of piston 102, i.e., that side upon which the coilform 120 is mounted. Part of the cooling gas is directed through the holes 99 in coilform 120, up through space 132 and the central bore 136 in pole piece 135 and through the radial bores 126, and out through the radially spaced passages 142 to the atmosphere. The remainder of the cooling gas passes through spider 122, between the windings on coilform 120 and top plate 115 and then out through passages 142 to the atmosphere. The two halves 100 and 101 of diaphragm 24 are represented by a single line in the schematic diagram shown in FIGS. 1, 5 and 9, and they seal off the portion of the inside of housing 106 into which the cooling air is directed from the portion of the inside of the housing 106 to which the line 82 is connected The sealing of the two portions of the inside of the housing 106 from each other, and the direction of the cooling gas through and around the coilform 120 and pole piece 135 provides continuous and highly effective cooling of the linear motor 23, regardless of the amount of power applied to the windings of the coilform 120. Actual experimentation has shown that power levels of over 400 watts have been applied to the coilform 120 without significant increase in the temperature of the linear motor 23 or anything mounted therein.

Piston 102, with the diaphragm 24 attached, seals the first side of the space within housing 106 from the other side of piston 102. The housing 106 of the embodiment of driver 23 shown in FIG. 7 is provided with restrictions, in the form of passages 142 and inlet 124, which constitute a chamber on the first side of piston 102 in which pressure is elevated by approximately 3 cm H$_2$O relative to atmospheric pressure. The effect of this elevated pressure is that, when patient airway pressures are sufficiently low, i.e., below about 15 cm H$_2$O, the increased pressure on the first side of piston 102 is adequate to maintain the desired characteristics of the polar pressure wave, any change in the slope or amplitude of the polar pressure wave being clinically insignificant. The resistance to the axial movement of coilform 120 provided by spiders 122 and 123 cooperates with the elevated pressure on the first side of piston 102 to prevent significant alteration of the polar pressure wave when patient airway pressures are below about 15 cm H$_2$O. Above that pressure, the effects of patient airway pressure alter the characteristics of the polar pressure wave produced by the driver 23 shown in FIG. 7, resulting in a decrease in the efficiency of that driver 23. Consequently, the driver 23 shown in FIG. 6, which operate to equalize the pressures on both sides of piston 102, was constructed to minimize the effect of patient airway pressure on the polar pressure wave produced by that driver.

Equalization of the pressures on both sides of piston 102 is important because, as the pressure on the second side of piston 102 increases, without a corresponding increase on the first side of piston 102, more force is required to move piston 102 toward the patient, i.e., away from magnet 117 while maintaining the same displacement of piston 102. Conversely, a reduction in pressure on the second side of piston 102 reduces the amount of force needed to move piston 102 toward the patient and increases the amount of force required to move piston 102 away from the patient, i.e., toward magnet 117. Since the electrical square wave delivered to coil 120 is controlled by controls 15, 15a or 20 (channel 1) or 16, 16a or 21 (channel 2) as shown in FIG. 2, the characteristics of the pressure wave produced by piston 102 may be selected by the operator. However, the effect of unequalized pressures on both sides of piston 102 is that piston 102 travels for a longer (or shorter) time in one direction than in the other, due also to the spring effect of spiders 122 and 123 Since the amount of force delivered to piston 102 remains constant for a given set of control settings, the changes in pressure on both sides of piston 102 change the slope of the leading and trailing edges of the pressure wave produced by piston 102, decreasing the efficacy of the driver 23. An important feature of the construction of driver 23 shown in FIG. 6 is its ability to produce a polarized pressure wave which is relatively free of the effect of the pressures developed on both sides of piston 102

Referring to that figure, driver 23 includes the two halves 100 and 101 of diaphragm 24 mounted therein, and piston member ! 102 The diaphragm 24 is connected to piston member 102 by retaining ring piston flange 103 through a plurality of screws, 104 and 105 being shown.

Figure 8B:
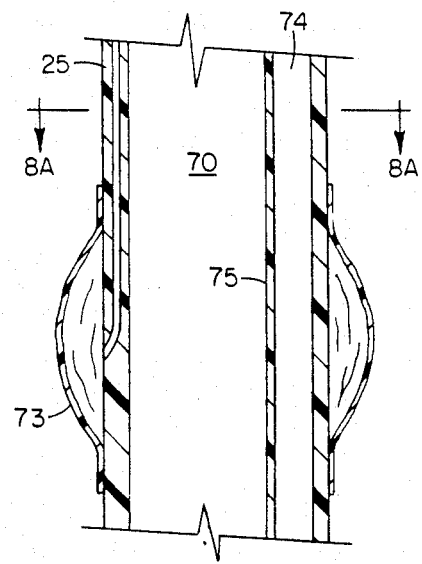
FIG. 8B is a longitudinal section through the endotracheal tube of FIG. 8A taken at the line 8B—8B in FIG. 8A.

Driver 23 includes a housing member 106 having a flange 107. The flange 107 connected to flange 108 of the outlet plate 110 by a plurality of screws 109. The two halves 100 and 101 of diaphragm 24 are clamped between the flanges 107 and 108 and, as shown in FIGS. 6, 7 and 8, each include a concave portion 112 to allow for their movement. The two halves 100 and 101 are used to help insure the accurate conversion of the electrical square wave signal to a polar pressure wave in gas conducting means 25 and to prevent the flapping of the diaphragm 24 under certain operating conditions.

Outlet plate 110 is bolted onto housing member 106 by a plurality of screws 109. The two halves 100 and 101 of diaphragm 24 are made of flexible rubber material and provide a seal between the flange 107 and flange 108. A fitting 113 is provided in the outlet plate 110 to which tube 25 is connected.

A top plate 115 is connected to the housing 106 by a plurality of screws 116. A magnet 117 is mounted between the top plate 115 and the back plate 118. A plurality of screws or bolts 119 connect the back plate 118 to the top plate 115 to clamp magnet 117 therebetween.

A coilform 120 is connected by a plurality of screws 121 to the piston member 102. The coilform 120 constitutes a moving mass.

Spiders or radial limiters 122 and 123 are glued or other wise affixed to the housing 106 and the moving mass 120 and allow axial movement while preventing radial movement.

Position sensor means 128 extends through bore 136 and is connected thereto by screw means 137 through a hole (not numbered) in plug 127. Position sensor means 128 is provided with a LED 129 and an infrared transistor 130. As the coilform 120 moves up and down, so does the piston member 102, and the distance. between piston member 102 and infrared transistor 130 is detected This distance designates the position of the piston member 102 and diaphragm 24 at all times. A lead 131 is connected with the position sensor means 128 for conveying power thereto and a signal therefrom. Lead 131 passes through strain relief 133 in the cone-shaped portion 145 of casing 156 and then through strain relief 134 in casing 156 as it passes out of regulator 121.

Electrical leads 138 and 139 connect to a terminal block 140 attached by screw 141. The terminal leads 138 and 139 are then connected to the coil or winding on coilform 120. As will be apparent, the upper end 120' of the coilform extends through the space 132 between the pole piece 15 and the top plate 115 to allow up and down, reciprocating motion of the coilform. The current in the coil form 120 moves in two directions by reversing the current, which causes the reciprocating motion of the linear motor.

Housing 106 is provided with a threaded inlet 124 for the receipt of a fitting 125 to which gas conducting means, or line 60 (see FIG. 9) may be attached, thereby connecting the space within the housing 106 on the first side of diaphragm 24 to a gas source 50 (see FIG. 9). A plurality of holes 99 are provided through the coilform 120 to allow the passage of gas from the gas source 50 (see FIG. 9) through the coilform 120. As noted above, pole piece 135 is provided with a plurality of radially extending bores 126 connecting with the central bore 136 and the radially spaced passages 142. Space 132 is also provided on both sides of coilform 120 between the, edges of top plate 115 to allow the passage of cooling gas around coilform 120.

The radially spaced passages 142 in pole piece 135 are covered by the cone-shaped portion 145 of casing 156. Casing 156 1 is provided with an outlet 147 formed by the flanges 159. Flanges 159 may be provided with threads or a fitting to allow the attachment of an exhaust or outlet tube if necessary. The cone-shaped portion 145 of casing 156 is provided with an orifice 146 in close proximity to an inflatable balloon 148. Balloon 148 is mounted on the circular raised portion 149 of cap 143 by being stretched over the raised portion 149 and held in place with an 0-ring 151 which rests in the annular groove 153 around the raised portion 149 of cap 143. The balloon 148 defines a space which is confluent with the bore 155 through cap 143. Fitting 157 is provided in the bore 155 to receive the line 28 which is connected to connecting means, or tube 25.

To better understand the operation of the valve formed by the balloon 148 and the orifice 146, it is necessary to examine the operation of the oscillating ventilator 10 having driver 23 shown in FIG. 6 incorporated therein, under both static and dynamic conditions by reference to FIG. 9, in which the driver 23 shown in FIG. 6 is shown schematically in shadow lines. If blower 50 is operated without moving piston 102 back and forth within the housing 106 and with valve 78 open, the flow of gas will be directed to tube 25 through lines 52 and 58. A portion of the flow will also be directed into the line 60 to serve as cooling gas. The cooling gas passes through the pressurizing orifice 86, through the inlet 124, and into the interior of housing 106 on the second side of diaphragm 24. At this point, the balloon 148 will not be inflated at all, allowing the cooling air to pass out of orifice 146 through outlet 147 to the atmosphere.

The next step is to adjust the valve 78 until a pressure of, for instance, 10 cm H$_2$O is created in tube 25. This increase in pressure will also be felt in the sensor tube 28, causing the balloon 148 to expand because of the pressure coming into the space behind balloon 148 through the cap 143. As the, balloon 148 expands, a portion of the orifice 146, is covered decreasing the amount of cooling air which can pass through the orifice 146, thereby causing an increase in pressure between the inlet 124 and the orifice 146.

When the circuitry is activated to cause piston 102 to move back and forth within the housing 106, and piston 102 moves in a direction away from the pole piece 135, the movement of piston 102 causes a pressure pulse to be delivered to tube 25 and also to the line 28. Balloon 148 responds to that pulse, tending to close off orifice 146, creating a reduced orifice size through which the cooling gas can escape and which allows the blower 50 to pressurize the first side of piston 102. As piston 102 continues in that direction, the pressure on the second side of piston 10 2 increases because of the compliance of the patient's lungs and the valve 78, which is still partially closed. This increase in pressure is likewise reflected as an increase in pressure in the sensor line 28, which causes the balloon 148 to further close off orifice 146, which causes the pressure on the first side of the piston 102 between the orifice 146 and the inlet 124 to increase even more. When the piston 102 moves in the opposite direction, i.e. back toward the pole piece 135, the pressure in tube 25 and in the lungs decreases, which allows the pressure in sensor line 28 to decrease, allowing the balloon 148 to contract so that the air inside the housing 106 between inlet 124 and orifice 146 will escape through orifice 146, allowing the pressure on the first side of the piston 102 to decrease, thereby equalizing the pres sure on both sides of the piston 102. The changes in pressure on both sides of the piston 102 are in phase; in other words, when pressure on the first side of piston 102 increases, so does the pressure on the second side, and when pressure on the first side of the piston 102 decreases, so does the pressure on the second side.

It is not necessary to equalize the pressure on both sides of piston 102 exactly to achieve the goal of faithfully translating the polar electrical signal into a polarized pressure wave in the gas, a fact which makes it possible to prevent the attenuation of the pressure wave at low patient airway pressures (below about 15 cm H$_2$O) merely by allowing the flow of cooling air produced by blower 50 to escape through the passages 142 in pole piece 135 to the atmosphere as discussed above. This apparatus is illustrated in FIG. 7.

Each of the alternative drivers 23 shown in FIGS. 6 and 7 is used over a different range of mean airway pressures. For instance, the driver 23 shown in FIG. 7 can best be used to advantage to support a patient with healthy lungs where mean airway pressures are about 10 to 15 cm H$_2$O. The driver 23 of FIG. 6, having regulator 121 attached thereto, can be used to manage a patient at mean airway pressures of from about 3 up to about 30 cm H$_2$O. Pressures in this range are useful in managing, for instance, human neonates suffering from hyaline membrane disease or patients with compromised or damaged lungs.

The amount of bias flow is controlled by adjusting valve 66 with control knob 69. Flowmeter 67 is provided, marked off in liters per minute, to allow the setting of the bias flow at a desired level. Bias flow levels of from about 2 to about 20 liters per minute may be used to advantage, depending upon the body weight of the patient, the amount of dead space and whether there is any leakage in the system. A bias flow rate of about 5 liters per minute is a preferred rate at which to start, then the rate of bias flow may be adjusted up or down for the particular circumstances of the patient being ventilated.

The present invention can also be used advantageously to administer anesthetic agents and other medications. When used, for instance, to administer anesthetic agents, the high frequency oscillating ventilator 10 will use only about 30 to 40% of the amount of anesthetic agent required when anesthesia is administered using conventional units. The anesthetic agent is introduced into the bias flow in line 26 at the point at which humidifier 62 is shown, and as discussed above, the amount may be periodically varied as may be required by adjusting valve 64. Within a few seconds of being attached to the high frequency oscillating ventilator 10, the patient will stop breathing. If breathing does not stop within about 30 seconds, and all fittings and connections have been made properly, the percent power may be increased by 10% or more anesthetic added, as the case may be. The patient should be monitored during the procedure for proper ventilation as well as the level of anesthesia. Should the partial pressure of carbon dioxide in the blood ($PCO_2$) be high, patient may begin to breathe against the ventilator, in which case the percent power is increased by 10%. At the end of the period of time for which anesthesia is required, the high frequency oscillating ventilator 10 can be used to wash out, or purge, the anesthetic agent from the patient merely by closing valve 64, increasing the bias flow and percent power, and allowing the ventilator to continue to run. Using this method, recovery time can be reduced to just a few minutes.

The high frequency oscillating ventilator 10 can also be used for respiratory therapy. For instance, patients with diseased or comprised lungs can be managed effectively by using low (i.e., below 15 cm $H_2O$) pressures and high power. Further, if a patient is not respiring as expected, the cause may be that a low recent activity level has caused some of the alveoli to partially deflate such that they do not participate in the respiratory function. These alveoli can be recruited by raising the mean airway pressure by 20 cm $H_2O$ for a few seconds and then allowing the pressure to return to its initial setting.

Probably the most important therapeutic feature is the capability to facilitate mucociliary transport, which is used at the first sign of pulmonary edema or lung insufficiency. The ventilator can be adjusted for mucociliary transport without disturbing ventilation or anesthesia levels. Doing so generally requires higher percent power settings, for instance, in the range of about 75 to 80%. Frequency is set at between about 10 and about 14 Hz, and the percent inspiration control knob 15a or 16a for the particular channel is then adjusted up and down from about 30 to about 70% until moisture droplets may be observed moving upwardly through gas conducting means 25. The control knobs 15, 15a and 20 may be set so that channel one will ventilate the patient normally for a period of time selected by control knob 29 and channel two may then be set for mucociliary transport for a selected period of time under the influence of control knob 30, with the ventilator 10 automatically cycling between channels one and two under the influence of switch SW.

The high frequency oscillating ventilator 10 is so effective that some subjects, after therapy or washout, will not begin breathing immediately after being taken off the ventilator. How ever, the patient will begin normal breathing when the $PCO_2$ and pH levels of the blood return to normal.

The apparatus of the present invention may be better under stood by referring to the following examples, which are provided by way of exemplification, and not limitation.

Two apparently healthy cats and six apparently healthy dogs were managed using the apparatus of the present invention with a linear motor 23 as shown in FIG. 7. The blood gases of the animals were analyzed on a Corning Model 178 self-calibrating blood gas analyzer. Table 1 lists the details of the results obtained from each patient. Each experiment is listed using the weight of the patient to identify the experiment.

Although the invention has been described in terms of the above-illustrated preferred embodiments, it is expected that changes may be made to these embodiments by those skilled in the art who have the benefit of this disclosure without departing from the spirit of the present invention, the scope of which is determined by the following claims.

TABLE 1

| CAT | | | | | | DOG | | | | | | |
| --- | --- | --- | --- | --- | --- | --- | --- | --- | --- | --- | --- | --- |
| 6 | 10 | 22 | 30 | 30 | 37 | 45 | 45 | 45 | 48 | 48 | 72 | Weight of animal (lbs) |
| 2.5 | 3.0 | 6.0 | 8.0 | 8.0 | 14.0 | 10.0 | 10.0 | 10.0 | 9.0 | 9.0 | 14.0 | Endotracheal tube size (mm) |
| 2 | 2 | 3 | 4 | 4 | 7 | 7 | 7 | 7 | 5 | 5 | 8 | Flow rate of respiratory gas (liters/min) |
| 10 | 10 | 10 | 10 | 10 | 10 | 10 | 10 | 10 | 10 | 10 | 10 | Airway Pressure (cm $H_2O$) |
| 14 | 14 | 14 | 14 | 35 | 35 | 14 | 21 | 28 | 14 | 35 | 14 | Ventilator frequency (Hz) |
| 50 | 50 | 50 | 50 | 50 | 50 | 15 | 50 | 50 | 50 | 50 | 50 | Percent inspiration |
| 40 | 40 | 30 | 30 | 50 | 50 | 30 | 37 | 44 | 40 | 60 | 40 | Percent power |
| 7.40 | 7.38 | 7.38 | 7.41 | 7.36 | 7.20 | 7.07 | 7.40 | 7.39 | 7.37 | 7.34 | 7.34 | pH of blood |
| 22.4 | 26.7 | 25.2 | 32.1 | 43.6 | 46.4 | 29.5 | 31.7 | 36.5 | 28.8 | 32.4 | 43.5 | Partial pressure of arterial $CO_2$($PCO_2$) |
| 97.8 | 135.8 | 96.4 | 103.9 | 119.6 | 100.3 | 135.0 | 89.6 | 93.2 | 104.7 | 94.3 | 97.9 | Partial pressure of arterial $O_2$ ($PO_2$) |
| 98.9 | 99.3 | 98.4 | 98.0 | 98.2 | 95.2 | 97.2 | 96.3 | 96.5 | 98.1 | 95.4 | 97.7 | Percent of possible blood $O_2$ saturation |

What is claimed is:

1. A method of ventilating a patient comprising:
   simultaneously delivering a flow of gas to both the first and the second sides of a piston which is diaphragmatically sealed in an oscillator;
   directing the flow of gas delivered to said first side of said piston through a means for moving said piston back and forth within said oscillator, thereby cooling said oscillator;
   moving said piston a selected distance back and forth within said oscillator, thereby creating a polar pressure wave in said flow of gas delivered to said second side of said piston;
   directing the flow of gas delivered to said second side of said piston into the lungs of a patient; and
   venting the flow of atmosphere directed into the lungs of the patient to the atmosphere.

2. The method of claim 1 wherein the pressures developed by the delivery of said flow of gas to both sides of said piston increase and decrease simultaneously on both sides of said piston while said piston is moving back and forth.

3. The method of claim 1 wherein the flow of gas directed through the means for moving the piston is thereafter exhausted to the atmosphere to cool said piston.

4. The method of claim 3 additionally comprising regulating the amount of the gas which is directed through the means for moving the piston which is exhausted to the atmosphere.

5. The method of claim 4 wherein the amount of the gas which is directed through the means for moving the piston and exhausted to the atmosphere is decreased when the pressure on the second side of the piston increases and increased when the pressure on the second side of the piston decreases.

6. The method of claim 1 wherein the pressure on the second side of the piston is maintained at a mean pressure of from about 3 to about 30 cm $H_2O$.

7. The method of claim 1 wherein said gas is delivered at a rate of about 2 to about 20 liters per minute.

8. The method of claim 1 wherein said piston is moved back and forth at a rate of from about 30 to about 12,000 times per minute.

9. The method of claim 1 wherein said piston is moved back and forth at a rate of from about 30 to about 3000 times per minute.

10. The method of claim 1 wherein an anesthetic gas is added to the flow of gas which is directed to the patient.

* * * * *

UNITED STATES PATENT AND TRADEMARK OFFICE
CERTIFICATE OF CORRECTION

PATENT NO. : 4,805,612

DATED : February 21, 1989

INVENTOR(S) : Robert L. Jensen

It is certified that error appears in the above—identified patent and that said Letters Patent is hereby corrected as shown below:

Column 8, line 22, change "present" to --percent--.
Column 8, lines 23-24, change "engages" to --changes--.
Column 8, line 26, change "o" to --on--.
Column 8, line 33, change "152" to --15a--.
Column 8, line 33, change "162" to --16a--.
Column 8, line 44, change "increase" to --increases--.
Column 8, lines 46 and 47, change "increase to --increases--.
Column 8, line 49, change "increase" to --increases--.
Column 9, line 23, after "Hz.", add --The percent inspiration for channels 1 and 2 is about 25%-75%.--.
Column 11, line 67, change "f" to --of--.
Column 12, line 34, delete "1".
Column 14, line 16, after "rectifier", add --(SCR)--.
Column 15, line 23, change "47 to --477--.
Column 15, line 67, delete "will".
Column 15, line 67, change "proceed" to --proceeds".
Column 16, line 54, delete "pro".
Column 16, line 54, after "which", add --proceeds through line 60 as compared to that portion--.
Column 18, line 60, change "15" to --135--.
Column 19, line 13, after "156", delete "1".

Signed and Sealed this

Fifth Day of December, 1989

Attest:

JEFFREY M. SAMUELS

Attesting Officer  Acting Commissioner of Patents and Trademarks